United States Patent [19]
Linker et al.

[11] Patent Number: 5,915,268
[45] Date of Patent: Jun. 22, 1999

[54] VERTICAL FLOW CHEMICAL DETECTION PORTAL

[75] Inventors: Kevin L. Linker; David W. Hannum, both of Albuquerque, N.M.; Frank James Conrad, Russellville, S.C.

[73] Assignee: Sandia Corporation, Albuquerque, N.M.

[21] Appl. No.: 08/995,777

[22] Filed: Dec. 22, 1997

[51] Int. Cl.[6] .............................. G01N 31/00; G01N 1/14
[52] U.S. Cl. ............................ 73/23.2; 73/28.01; 422/93
[58] Field of Search .................... 73/23.2, 23.36, 73/86.03, 863.71, 23.31, 28.01; 422/93, 94

[56] References Cited

U.S. PATENT DOCUMENTS

| | | | |
|---|---|---|---|
| 3,725,895 | 4/1973 | Haynes | 340/280 |
| 3,942,357 | 3/1976 | Jenkins | 73/23 |
| 4,045,997 | 9/1977 | Showalter et al. | 73/23 |
| 4,195,513 | 4/1980 | Cohen | 73/23 |
| 4,202,200 | 5/1980 | Ellson | 73/23 |
| 4,909,089 | 3/1990 | Achter et al. | 73/863.11 |
| 4,964,309 | 10/1990 | Jenkins | 73/864.81 |
| 4,987,767 | 1/1991 | Corrigan | 73/23.36 |
| 5,018,395 | 5/1991 | Hickox et al. | 73/864.34 |
| 5,092,218 | 3/1992 | Fine et al. | 86/50 |
| 5,109,791 | 5/1992 | Corrigan | 73/23.36 |
| 5,162,652 | 11/1992 | Cohen | 250/288 |
| 5,345,809 | 9/1994 | Corrigan | 73/23.2 |
| 5,395,589 | 3/1995 | Nacson | 422/88 |
| 5,465,607 | 11/1995 | Corrigan | 73/23.36 |
| 5,469,369 | 11/1995 | Rose-Pehrsson et al. | 364/497 |
| 5,585,575 | 12/1996 | Corrigan et al. | 73/863.71 |

OTHER PUBLICATIONS

J. E. Parmeter, et at., "Testing of a Walk–Through Portal for the Trace Detection of Contraband Explosives", Apr. 1997.

*Primary Examiner*—Hezron Williams
*Assistant Examiner*—J. David Wiggins
*Attorney, Agent, or Firm*—Russell D. Elliott

[57] ABSTRACT

A portal apparatus for screening objects or persons for the presence of trace amounts of chemical substances such as illicit drugs or explosives. The apparatus has a test space, in which a person may stand, defined by two generally upright sides spanned by a horizontal transom. One or more fans in the transom generate a downward air flow (uni-directional) within the test space. The air flows downwardly from a high pressure upper zone, past the object or person to be screened. Air moving past the object dislodges from the surface thereof both volatile and nonvolatile particles of the target substance. The particles are entrained into the air flow which continues flowing downward to a lower zone of reduced pressure, where the particle-bearing air stream is directed out of the test space and toward preconcentrator and detection components. The sides of the portal are specially configured to partially contain and maintain the air flow.

23 Claims, 3 Drawing Sheets

VERTICAL FLOW CHEMICAL DETECTION PORTAL

The Government has rights to this invention pursuant to Contract No. DE-AC04-94AL85000 awarded by the U.S. Department of Energy.

BACKGROUND OF THE INVENTION

1. Field of the Invention (Technical Field)

The present invention relates to apparatus for detecting substances, particularly controlled or dangerous substances, and specifically for detecting small quantities of substances upon a person or object.

2. Background Art

The continued use of explosives by terrorists has prompted the United States Federal Aviation Administration and similar organizations worldwide to pursue the development of various explosives detection systems for the screening of airline passengers and baggage. The use of traditional x-ray based systems for bulk detection has fallen into some disfavor due to significant privacy and public health concerns. In the case of screening persons, moreover, trace detection systems, rather than bulk detection, are of increasing interest for the identification of individuals who recently have handled explosives materials, to alleviate the added risk such persons may pose to mass transit passengers. Any apparatus or method for detecting trace amounts of a particular substance on persons must be relatively non-invasive and physically innocuous—preferably involving no physical contact—so as not unduly to infringe upon the physical privacy of the person being screened.

Any practicable detection apparatus must also be capable of rapid operation. Particulate collection by wiping or brushing a surface to be tested improves reliability of the test, but consumes too much time on a per-test basis to be practical in busy international airports and the like. An effective detection apparatus accordingly must be capable of completing an entire test cycle in a matter of a few seconds, but also must be able reliably to perform numerous test cycles repeatedly for prolonged periods of time. Thus, few moving parts and simplicity of structure and operation are demanded for long-term durability after thousands of test cycles.

Thus, a viable explosives detection portal must overcome at least two primary impediments. First, a practical detection device must accommodate the physical properties of explosives chemicals that make explosives vapor detection difficult, namely, the extremely low vapor pressure of explosives commonly used by terrorists. For example, pentaerythritol tetranitrate (PETN), cyclonite (RDX), C-4, and Semtex, potent and commonly used explosives, have vapor pressures of only a few parts per trillion under standard pressure and temperature. Low vapor pressures compel the use of highly sensitive detectors in the apparatus.

Additionally, a practical detector must have a very short screening time. It is widely believed that a commercially acceptable detection portal must screen people at a rate of no more than about ten seconds per person in order to screen all persons using the typical airport boarding concourse without unacceptable delay and frustration. Due to the time constraint, the problem of low explosives vapor pressure cannot be overcome merely by increasing the length of time the explosives vapors/particles are collected in the portal detector.

Currently, explosives detection at large airports and other facilities is performed mainly by the use of bomb-sniffing dogs. The use of dogs nevertheless has proven to be too time consuming and somewhat unpredictable as a long-term solution for safeguarding the traveling public.

The traveling public is accustomed to the use of portal-type metal detectors, which detectors require no physical contact and little time to operate and thus serve as a plausible paradigm for explosives detection as well. A need remains, therefore, for a "walk-through, no-contact" detection portal apparatus through which persons and/or objects may quickly be passed, yet which reliably detects the presence on the person or object of dangerous chemicals such as explosives or illegal drugs.

Against the foregoing background, the present invention was developed. The detection portal described below overcomes the significant impediments posed to a walk-through explosives detection portal.

SUMMARY OF THE INVENTION
(DISCLOSURE OF THE INVENTION)

The invention relates to a chemical detection portal apparatus for screening objects or persons for the presence of particles of target substances such as drugs, explosives (which, as mentioned previously, may have low vapor pressure), or the like.

In accordance with the invention there is provided an apparatus for screening an object for the presence of a target substance thereon, comprising a detector, means for generating a downward flow of air from a zone above the object to a zone below the object whereby particles of the substance on the object are dislodged therefrom and become entrained in the flowing air, and means for moving the air with entrained particles from the zone below the object to the detector. The detector preferably comprises an ion mobility spectrometer. The preferred embodiment further comprises means for partially containing the downward flow of air, the means for partially containing the downward flow of air preferably comprising a walk-through portal, said portal comprising two sides and a transom extending substantially horizontally between the respective tops of said sides, whereby said sides and said transom define therebetween a test space. The means for generating a downward flow of air comprises at least one fan in the transom. The preferred embodiment also further comprises air jet nozzles disposed in said sides for blowing air laterally within said test space. Each of said sides preferably comprises a substantially vertical inside wall, a sloped wall below and connected to said inside wall, and a substantially vertical bottom wall below and connected to said sloped wall, whereby said zone above the object is defined at least in part by said inside walls, and said zone below the object is defined at least in part by said bottom walls, said zone above comprising a larger volume than said zone below. Also, the means for moving the air with entrained particles preferably, comprises a fan in at least one of said sides, and at least one vent intake disposed in at least one of said bottom walls.

Also in accordance with the invention there is provided a portal apparatus for screening an object for the presence thereon of target particles, said portal apparatus comprising two generally vertical sides, a transom extending substantially horizontally between the respective tops of said sides, whereby said sides and said transom define therebetween a test space, means in said transom for generating a downward flow of air into said test space and between said sides, a particle detector, and means for moving air from within the test space to said particle detector. In this embodiment, each of said sides comprises: a substantially vertical inside wall;

a sloped wall below and connected to said inside wall; and a substantially vertical bottom wall below and connected to said sloped wall, whereby said inside walls are spaced further apart than said bottom walls, thereby narrowing said test space from top to bottom. The means for generating a downward flow of air comprises at least one fan for blowing ambient air, while the means for moving air from within the test space optionally comprises a fan in at least one of said sides, and at least one vent intake disposed in at least one of said bottom walls.

Still further in accordance with the invention there is provided a portal apparatus for screening an object for the presence thereon of trace amounts of a target substance, said apparatus comprising means for generating a downward flow of air past the object whereby particles of the substance on the object are dislodged therefrom and become entrained in the flowing air, and means for partially containing the flowing air to direct the air towards a detector. The means for partially containing preferably comprises two upright sides in spaced-apart relation, each of said sides comprising at least one sloping wall whereby the distance separating said sides decreases from the tops of said sides to the bottoms of said sides, a transom extending substantially horizontally between and connecting respective tops of said sides, whereby said sides and said transom define therebetween a test space. The means for generating a downward flow of air preferably comprises a pair of fans disposed in said transom. Each of said sides preferably comprises: a substantially vertical inside wall; a sloped wall below and connected to said inside wall; and a substantially vertical bottom wall below and connected to said sloped wall, whereby said zone above the object is defined at least in part by said inside walls, and said zone below the object is defined at least in part by said bottom walls, said zone above comprising a larger volume than said zone below. The preferred embodiment optionally further comprises air jet nozzles disposed in said vertical inside walls for blowing air laterally within said test space. The detector preferably comprises an ion mobility spectrometer.

A primary object of the present invention is to provide a chemical detection apparatus that is amenable for use in public places or private manufacturing or research facilities for screening persons or objects for the presence of target or contraband substances.

A primary advantage of the present invention is that it permits persons to be screened with little or no physical contact.

Another advantage of the invention is that it may be repeatedly operated with a very short cycle time.

Still another advantage of the invention is that it is an apparatus that is simple and relatively portable yet reliable.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
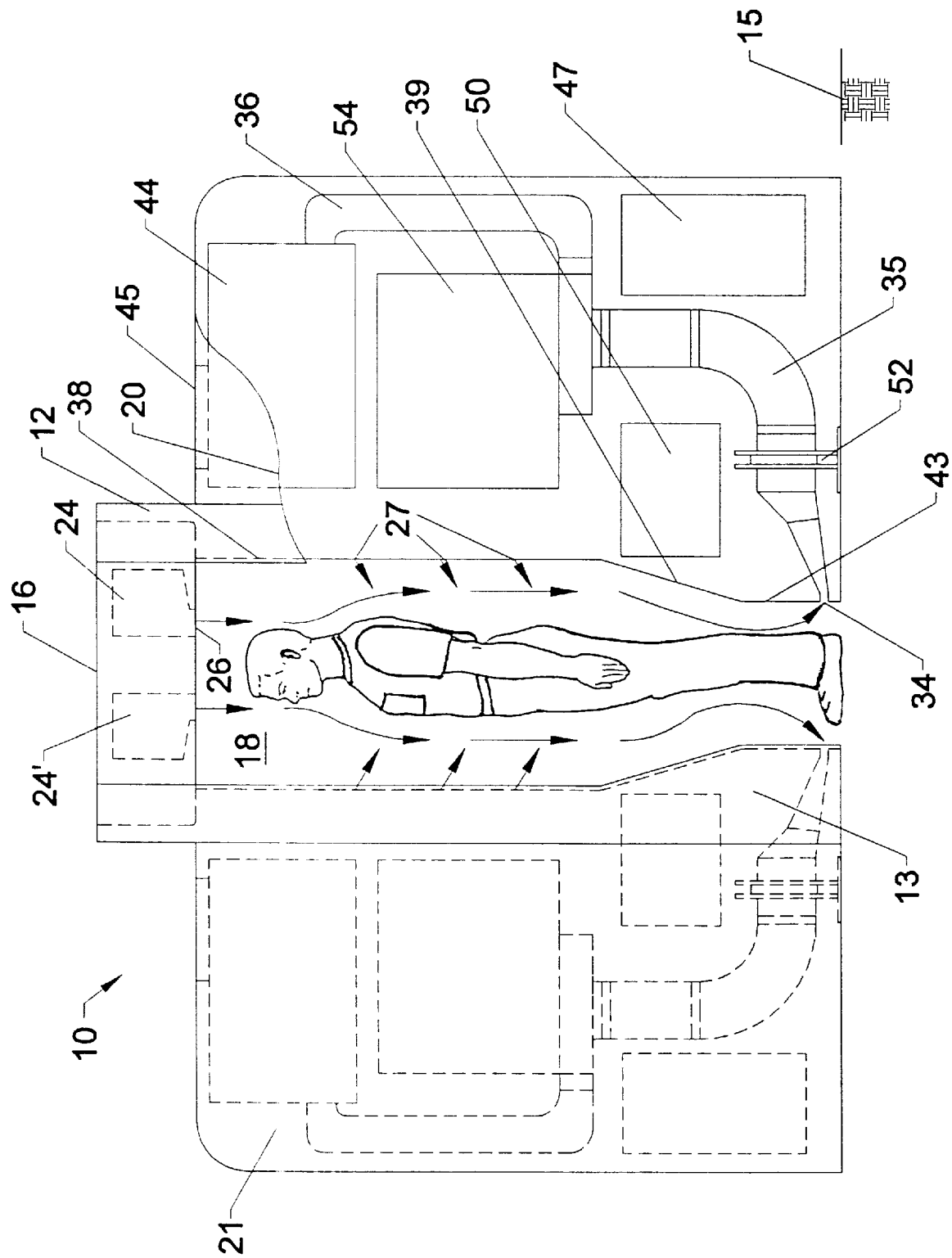
FIG. 1 is a front view in elevation of a preferred embodiment of the invention, with a portion broken away to show certain interior elements.

DESCRIPTION OF THE PREFERRED EMBODIMENTS (BEST MODES FOR CARRYING OUT THE INVENTION)

The invention relates to an apparatus for detecting substances, such as illegal drugs and explosives, on persons and objects, particularly pedestrians. The apparatus is contemplated for use especially at facilities where security from drugs and explosives is of utmost importance, such as airport terminals, penitentiaries, and the like. Accordingly, the primary intended use of the invention is the detection of very small amounts of contraband substances such as explosives or narcotics in an effort to prevent the passage of the contraband substances into a secured area. Nevertheless, it is readily understood that the invention may find useful application for in the trace detection of other targeted or controlled substances for purposes of theft detection, environmental or occupational health, and other circumstances. The invention may be used to screen inanimate objects as well as people; in this specification, an "object" to be screened shall include persons and animals, as well as inanimate items. Also in the disclosure and in the claims, "target substance" means a particular substance sought to be detected, and includes but is not limited to narcotics, explosives, and their constituents and/or by-products. "Particle" means particulate matter of nearly any size, especially particulates sufficiently small as to be readily airborne, and includes but is not limited to droplets or dry motes, vapors and fumes, large molecules, and solid particles. "Target particles" refers to the particular type of particles to be screened for by the practice of the invention, and includes, by way only of example, explosives, drugs, nuclear material, and the like. Embodiments of the apparatus may be adapted to detect more than one target substance in a single pedestrian pass-though.

When a person prepares explosive devices or handles illicit drugs, trace amounts of the explosive or drug substances almost inevitably cling to the person's skin (especially the hands) and/or clothing. These residues typically are present in quantities too small for visual detection, perhaps even in such small quantities as to be undetectable by bomb- or drug-sniffing dogs. In practice, the invention utilizes air flow sampling of target substance vapor and particulate matter. The present invention permits trace quantities of a target substance clinging to a person or object to be swept from the person by a moving air stream and carried to a target particle detector. Additionally, if a person or item is concealing a bulk quantity of a targeted substance (such as a bomb or a bundle of narcotics), small quantities of particles and chemical vapors may emanate from the bulk quantity into the surrounding air, and thus be available for detection. An advantage of the invention is that personnel may be screened without any direct physical contact, and in this respect is similar to the metal detectors that are already widely used in airports and accepted by the general public as not unduly jeopardizing personal privacy.

Broadly described, a preferred embodiment of the invention includes a portal, very generally in the size and shape of a door frame, through which the objects/persons to be screened are passed, and an inventive air stream flow generator. When individual pedestrians are screened, they may simply walk through the portal, pausing briefly therein while the screening is performed. The apparatus is used in conjunction with a preconcentration system and trace chemical detectors. A moving air stream is generated which dislodges small particles clinging to a person (or item). Many or perhaps all of the particles may and will be innocuous and irrelevant, such as lint, pollen, dandruff, tobacco ash, or any other of the countless substances encountered and/or handled by a typical person on a given day. If the person recently has been handling or been in close contact with a target substance, however, particles of the target substance will also be dislodged and swept into the moving air stream. The moving air stream flows downward within the portal and past two sides (e.g. front and back) of the person being screened, and upon reaching the bottom of the portal is sucked laterally from within the portal. Any target substance particles from the person or object are immediately carried by the air flow to a preconcentrator for collection and retention. After a quantity of target substance particles has been allowed to accumulate in a preconcentrator, they are moved to a chemical detector, such as an ion mobility spectrometer, for detection.

A front view of a preferred embodiment of the portal apparatus is shown in FIG. 1. In this specification, "back" and "front" in correlation with the drawings shall correspond to directions "into" and "out of" the plane of the drawing paper, respectively. "Laterally" or "side" corresponds to the right and left directions orthogonal to front and back according to conventional meaning. The portal 10 incorporates a frame defined by two upright, generally vertical, sides 12, 13 whose respective tops are interconnected by a generally horizontal transom 16. The transom 16 and sides 12, 13, together with the floor 15 upon which the portal 10 rests, define a test space 18 in which the object or person to be screened is located during operation of the invention. Test space 18 thus is closed on top and bottom and two sides, but open to the front and back. In the preferred embodiment, two equipment modules 20, 21 are attached exteriorly to the sides 12, 13 to house functional components of the invention to be described. The preferred embodiment has a module 20 or 21 attached to each of two functional sides 12, 13, although alternative less desirable embodiments may have a single module 20 connected to a side 12 or 13.

Figure 2:
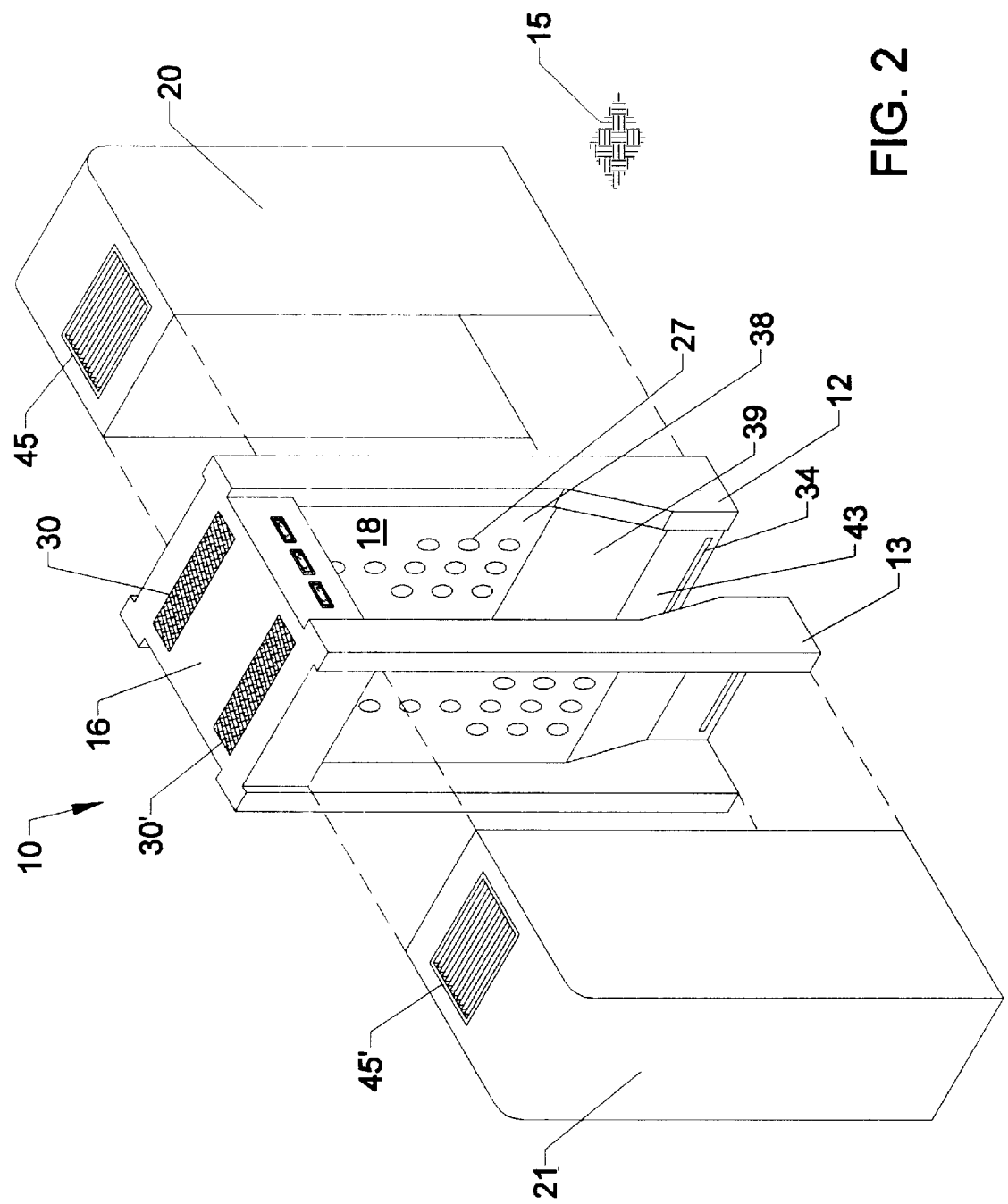
FIG. 2 is a partially exploded perspective view, from above, of the embodiment shown in FIG. 1.
Figure 3:
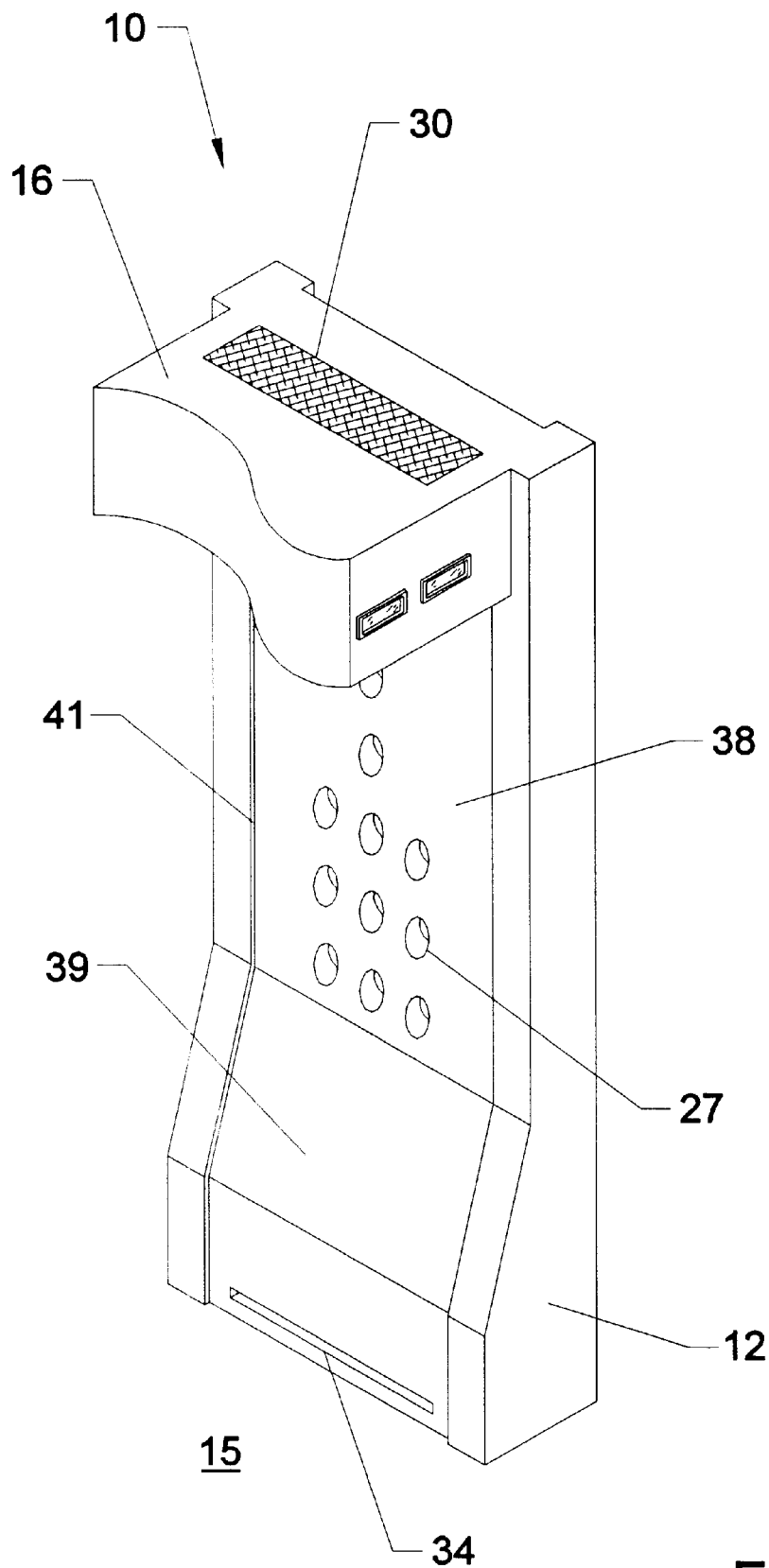
FIG. 3 is an enlarged view of a particular portion of the embodiment shown in FIG. 2.

The preferred embodiment of the portal 10 is sized to fit easily in the concourse of an airport terminal or the lobby of a courthouse, or the like, and may be quite portable. The test space 18 is sized to permit a person of any height to stand erect therein; in normal use, a person stands within the test space 18 between the sides 12, 13, and faces one of the sides 12 or 13 during the operation of the apparatus, as indicated in FIG. 1. In the preferred embodiment, the sides 12, 13 are about 78 inches high and about 34 inches wide (the dimension between the open front and back of the portal 10), but these dimensions are offered by way of example rather than by limitation. The sides 12, 13 are placed in generally parallel, spaced-apart relation. Each of the sides 12, 13 features an inside wall 38 and, below the inside wall, a bottom wall 43. As FIGS. 1–3 illustrate, the sides 12, 13 are shaped so that the bottom portions are thicker from side-to-side than the top portions, so that when the sides 12, 13 are placed in a mutually confronting position the bottom walls 43 are closer together than the upper inside walls 38. The bottom walls 43 of the sides 12, 13 below the sloped walls 39 (FIG. 3), preferably are separated by a distance of approximately 17 or 18 inches, while the inside walls 38 above the sloped portions 39 preferably are spaced apart a distance of approximately 27 inches. The transom 16 in the preferred embodiment has an overall length of about 39 inches, bridging a span of about 27 inches from side to side. All the foregoing dimensions are given by way of an example to disclose the respective proportions of one preferred embodiment; larger and smaller versions of the apparatus of the invention may be constructed with concordant adjustments being made to the air stream discharges generated by the apparatus.

Disposed within the transom 16 is at least one, and preferably two, supply fans 24, 24' for generating a, downward movement of air from the transom 16 toward the floor 15. Fans 24, 24' pull ambient air through intake vents 30, 30' from above the transom 16. The moving air optionally is passed through filters, and then is expelled through respective outlet vents 26 in the bottom of the transom 16, resulting in the generation of two downwardly directed air stream flows as generally depicted by the directional arrows of FIG. 1. In alternative embodiments employing a single supply fan, the fan and a single outlet vent are centrally located in the span of the transom 16. In the preferred embodiment illustrated in FIG. 1, the pair of outlet vents 26 are spaced on either side of the center of the transom 16 so as to approximately symmetrically split the flow of air on either side of the object being screened. In the case of a portal 10 designed to screen a person standing sideways in the test space 18, as illustrated in the figure, the vents 26 may be offset slightly toward one of the sides 12 to account for the assymetry of the person's situation in the test space 18 (attributable to the physiology of the human posture where the body is balanced generally above the heels, rather than the arches, of the feet).

FIGS. 1 and 3 depict the configuration of the sides 12, 13, which in the preferred embodiment are generally identical, but merely placed in confronting relation so that the inside walls 38 of each side 12, 13 are parallel opposite each other to define the test space 18 therebetween. In the preferred embodiment, description of one side 12 thus serves to describe both sides 12, 13, which are disposed in opposite positions upon the floor 15.

The inside wall 38 of a side 12 preferably is generally vertical, and descends from its intersection with the transom 16 to its intersection with the sloped wall or portion 39. Sloped wall 39 is disposed at an oblique angle down and away from inside wall 38.

The inside wall 38 and sloped wall 39 of respective sides 12, 13 accordingly are contoured as shown in FIG. 3 to direct air flow from, supply fans 24, 24'. The surfaces of the inside and sloped walls 38, 39 of the sides 12, 13, which may be somewhat concave, function substantially to confine between the sides 12, 13 the air flow from fans 24, 24', and also to constrict the air flow as it moves downward from the transom 16. As best seen in FIG. 1, the lateral distance separating the interior surfaces of the sides 12, 13 thus is constant in the volume between the respective inside walls 38, and then decreases as a function of the downward distance from the intersections of the inside walls 38 with the sloping walls 39.

In the preferred embodiment therefore, the movement of the air streams from the fans 24, 24' is mostly (but not entirely) confined within the space between the sides 12, 13, but moves into a zone of narrower cross-sectional area, with the result that flow velocities are partially maintained despite some air stream losses from the open front and back of the test space 18 of the portal 10. A substantial fraction of the air discharged from the fans 24, 24' ultimately obtains the floor level and enters into the respective floor vent intakes 34. It is seen, therefor, that the sides 12, 13, function to direct and partially contain the flow of air from the upper zone between the inside walls 38 to a lower zone, generally below the object being screened, between the bottom walls 43.

In the preferred embodiment, each of the two supply fans 24, 24' generates an air stream discharge of about 170 $ft^3/min \pm 10\%$; the preferred total initial downward velocity of air generated by the one or more fans 24, 24' thus is between about 270 ft/min and about 400 ft/min, most preferably about 340 ft/min. In the preferred embodiment of the portal 10 dimensioned as described above, total initial velocities below about 270 ft/min are generally inadequate to remove sufficient quantities of target particles from the test subject and transport them to the floor vent intakes 34. Conversely, we have determined that initial total velocities above about 400 ft/min cause undesirable turbulence in the air flow, resulting in excessive loss of air flow out the open front and back of the test space 18, with the attendant loss of any target particles entrained therein.

FIG. 1 shows a pair of modules 20, 21 disposed in adjacent relation to the two respective sides 12, 13. The right side module 20 is shown with a portion broken away to reveal certain interior components useable in the invention. Description of the one module 20 and its operation suffices to describe the other module 21, as the two are substantially identical; components of the right module 20 labeled and described herein thus describe as well the corresponding components of the left module 21 shown in phantom in FIG. 1. Each module 20, 21 encloses functional components utilized in the practice of the invention, including a vapor or particle preconcentrator 52, a particle detector 50, a power distribution center 47, and exhaust fan 54, and an exhaust port 45. Module 20 will be described, it being understood that description of components of that module also describes corresponding elements in the other module 21 used concurrently.

Summarily described, the flow of air through the module 20 is from the floor vent intake 34 to the exhaust port 45, with the movement of the air provided primarily by the effect of the exhaust fan 54. Air leaves the test space 18 and enters through the floor vent intake 34. The air, which has target particles entrained therein, moves to the preconcentrator 52, where the target particles are preconcentrated and retained for analysis by the detector 50. From the preconcentrator 52, air is pushed up the ducts 35, 36 and expelled from the module 20 via the exhaust port 45. A muffler 44 may be provided to muffle noise.

The movement of air out of the test space 18 is maintained by operation of exhaust blower fan 54, at least one of which is disposed in each of the modules 20, 21. In the preferred embodiment, the discharge generated by each of the exhaust fans 54 is between about 60 $ft^3/min$ and about 360 $ft^3/min$, most preferably about 330 $ft^3/min$, so that the total discharge from the bottom of the test space 18 and through both the floor vent intakes 34 most preferably is approximately 660 ft3/min. We have determined that total discharges in excess of about 720 ft3/min tend to induce a deleterious pressure drop through most preconcentrator devices, and/or pose some difficulty for a typical blower fan 54 (e.g. two fans each driven by a 2.0 horsepower motor) to develop the desired flow with a given pressure drop. Total discharges of less than about 120 ft3/min are insufficient to generate the necessary flow velocities to maintain defined air streams bearing entrained target particles from the test subject to the floor vent intakes 34.

We have determined that the performance of the apparatus as dimensioned herein is optimized when the face velocity of the air flow into each of the floor vent intakes 34 is approximately 2,000 ft/min. To develop and maintain such velocities, the floor vent intakes 34, which are located just above the level of the floor 15, have the shape of short, wide rectangles approximately 22 inches wide (measured parallel to the floor) and about 1 inch high. As previously mentioned, in the preferred embodiment the floor intake vents 34 are spaced apart laterally approximately 17 inches to 18 inches.

The fans 24, 24' and exhaust fans 54 are simultaneously operated for approximately 5.0 seconds while the test subject occupies the test space 18. With the discharge generated by the supply fans 24, 24' being substantially less than the discharge generated by the exhaust fans 54, concurrent operation of all the fans creates a zone of reduced pressure at the bottom of the test space 18, inducing a mass movement of air from the top of the test space toward the bottom thereof, e.g. from the volume just below the transom 16 to the volume adjacent the floor 15.

As shown by the directional arrows in FIG. 1, the use of two supply fans 24, 24' spaced apart in the transom 16 provides for a smooth flow of air downward past two sides (e.g. dorsal and ventral) of an individual standing within the test space 18. A stream of air flows downward from above the individual, and is bifurcated or deflected about his head and shoulders, and then flows, preferably at about 400 ft/min, down between the individual's torso and the sides 12, 13 toward the floor 15. Upon reaching the individual's feet in the proximity of the floor 15, the air streams are diverted laterally toward respective floor vent intakes 34.

The duct 35 leads from the floor vent intake 34 to the exhaust port 45. From its communication with the test space 18 between the sides 12, 13, the floor vent intake 34 is in communication with a preconcentrator 52. The preconcentrator 52 is a component for preconcentrating the target particles suspended in the air stream. Because the target particles ordinarily are present in extremely low concentrations within the air stream, it is preferable to preconcentrate the target particles, by collection, for presentation to the detector 50 in concentrations sufficiently high as to exceed the detector's functional threshold. While a large volume air stream is moved by the exhaust blower fan 54 from the floor vent intake 34 to the corresponding one of the exhaust ports 45, 45' (FIG. 2), target particles are collected by the preconcentrator 52 from the air moving through the duct 35.

Preconcentrator 52 may be any known type of device which collects target particles from the moving air stream until a sufficient quantity of target particles has been accumulated that they may be presented to the detector 50 in detectible quantities. Preconcentrator 52 may be, for example, a known charcoal absorption or thin-foil type device. Preferably, the preconcentrator is of the type disclosed in our copending application, entitled "Particle Preconcentrator" and having Ser. No. 08/988,342, the disclosure of which is hereby incorporated by reference.

A source of compressed air is employed to whisk the target particles accumulated in the preconcentrator 52 directly to the detector 50. Detector 50 is any of the devices known for detecting and/or measuring particles and/or particle concentrations. The detector 50 preferably is an ion mobility spectrometer (IMS), particularly if the invention is to be used to detect particles of explosives. A suitable ion mobility spectrometer for use in the invention is a sideflow PCP-110, manufactured by PCP, Inc., of West Palm Beach, Fla. Ion mobility spectrometers are a device known in the art of detecting dilute quantities of target particles. Other detectors suitable or adaptable for use in the invention include, without limitation: an Electron Capture Device (ECD), which can detect some explosives but perhaps not narcotics; gas chromatograph, chemiluminescence (both of which detection methods are less desirable for detecting particles of narcotics); mass spectrometer (suitable for detecting a wide variety of target particles, including explosives and narcotics); ITMS® (Ion Trap Mobility Spectrometer, for detecting both explosives and narcotics); and Thermo-Redox. The detector 50 provides to the operator a measurement of the concentration of target particles in the gas stream, as accumulated by the preconcentrator 52. In one embodiment of the invention, the detector 50 is connected to an audible or visual alarm in the event target particles are detected above a predetermined concentration.

Once the detector 50 has determined the presence or absence of a preselected concentration of target particles, the preconcentrator 52 and detector 50 are purged in preparation for a new testing cycle. The operation of the portal 10 may be controlled by means of controlled activation of the power distribution center 47, which control in the preferred embodiment is computer-aided. The actuation, duration of operation, and deactivation of the various operative components within each module 20, 21 are coordinated to provide for a rapidly repeated, cyclical operation of the portal 10 invention. It is optional, for example, to deactivate the fans 24, 24' and 54 between cycles when no person or object occupies the portal 10.

Optionally but preferably, a separate lateral flow of air toward the test subject and away from both inside walls 38 is provided by a plurality (for example nine to twenty) of air jet nozzles 27 symmetrically and centrally arranged within the inside wall 38, as best seen in FIGS. 2 and 3. The nozzles 27 are aimed radially inward toward the person in the portal 10 to generate streams of air blowing mildly laterally against the person. Jet nozzles 27 are in communication with a source of compressed air (e.g. a pressurized tank in the module 20, or one of the fans 24, 54), and are disposed in the wall 38 and aimed so as to blow moving air laterally directly against the individual or object being screened within the test space 18. Each nozzle 27 is designed to blow about 1.0 ft3/min, and thus function gently to agitate or rustle slightly the outerwear or surface of the person or object within the portal 10, which promotes the dislodging of target particles from the person or object. This "fluffing" or "frisking" effect of the nozzles 27 frees target particles from clinging to the screen person or item; the freed particles are then immediately entrained into the airstream flowing from the fans 24, 24' downward to the floor vent intakes 34 for evacuation and evaluation. The nozzles 27 may be adjustable air nozzles such as nozzle Model No. 48009 Adjustable Air Saver Nozzle available from Air Research Technology Company. These ARTX® nozzles are desirable for their advantage of air amplification, whereby the compressed air flow is amplified by entraining ambient air into the stream, delivering high thrust with just a fraction of the compressed air otherwise moving through the open air line. The movement of 1.0 ft3/min through each nozzle 27 thus is amplified to have the equivalent effect of a stream of about 25 ft3/min, promoting adequate agitation of the test subject's clothes, but without wasting compressed air or energy resources.

Upon entering the portal, a test subject turns ninety degrees and stands still for approximately 5.0 seconds while being screened. Air is blown by fans 24, 24' downward from the transom 16 into the test space 18 of the portal 10. The air stream bifurcates to flow along opposing sides of the person's body, between the person and the sides 12, 13 of the portal 10. Air flow rates along the person's body are typically about 400 feet/minute. The air stream movement downward is constricted and accelerated as the discharge moves from the larger volume in the upper zone between the parallel upper inside walls 38, transitions between the opposing non-parallel sloped walls 39, and moves into the comparatively confined lower zone between the parallel bottom walls 43. The overall effect of the operation of the portal 10 is to generate a pressure differential between the upper portion of the test space 18 and the lower portion thereof, so that air flows quickly and nearly exclusively in a downward direction from a zone of elevated pressure between inside walls 38 to a zone of reduced pressure between the bottom walls 43.

As the air streams flow downwardly past the subject being screened, target particles upon the subject are dislodged therefrom and become entrained and airborne within the airstreams. The lateral-blowing action of the nozzles 27 promotes the emanation of target particles from the surface (e.g. clothing) of the subject, as the air thrust from the nozzles 27 disturbs or perturbs molecules and particles clinging to the surface of the subject. The air streams bearing the entrained target particles continue downward to the zone between the bottom walls 43, where the target particle-bearing air is presented to the floor vent intakes 34.

Due to the forceful suction of the exhaust fans 54, air exits the test space 18 via the floor vent intakes 34 near the subject's feet. Under typical operating conditions, the volume flow rate of air into each vent 34 is about 330 ft$^3$/min. Upon exiting the test space 18, the air flows into the preconcentrator 52. The preconcentrator 52 allows air to pass through to a duct 36 while collecting heavy organic molecules such as explosives particles. The accumulated target particles then are selectively directed, preferably by a plug flow of air, into an IMS detector 50 for detection. In its preferred design, the portal 10 will have two preconcentrators 52 and two detectors 50, as suggested in FIG. 1.

The portal 10 accordingly is designed to screen personnel without any direct physical contact, and in this respect it is similar to the metal detectors that are already widely used in airports and accepted by the general public. The airflow sampling utilized is capable of collecting explosives material in the form of both vapor and particulate, the latter being potentially present on the exterior of a person's clothing in the form of fingerprint contamination. By practice of the invention, a total screening time of approximately twelve seconds per test cycle can be achieved.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for screening an object for the presence of a target substance thereon, the apparatus comprising:
    a detector;
    means for generating a downward flow of air from a zone above the object to a zone below the object, whereby particles selected from the group consisting of volatile particles of the target substance on the object which are dislodged therefrom by flow of air, non-volatile particles of the target substance on the object which are dislodged therefrom by flow of air, particles of the target substance present in air surrounding the object, and combinations thereof become entrained in the flowing air; and means for moving the air with entrained particles from the zone below the object to the detector.

2. An apparatus according to claim 1 wherein said detector comprises an ion mobility spectrometer.

3. An apparatus according to claim 1 further comprising means for partially containing the downward flow of air.

4. An apparatus according to claim 3 wherein said means for partially containing the downward flow of air comprises a walk-through portal, said portal comprising:

two sides; and a transom extending substantially horizontally between the respective tops of said sides, whereby said sides and said transom define therebetween a test space.

5. An apparatus according to claim 4, wherein said means for generating a downward flow of air comprises at least one fan in said transom.

6. An apparatus according to claim 4 further comprising air jet nozzles disposed in said sides for blowing air laterally within said test space.

7. An apparatus according to claim 4 wherein each of said sides comprises:

a substantially vertical inside wall;

a sloped wall below and connected to said inside substantially vertical wall; and a substantially vertical bottom wall below and connected to said sloped wall, whereby said zone above the object is defined at least in part by said inside walls, and said zone below the object is defined at least in part by said bottom walls, said zone above comprising a larger volume than said zone below.

8. An apparatus according to claim 7 wherein said means for moving the air with entrained particles comprises:

a fan in at least one of said sides, and at least one vent intake disposed in at least one of said bottom walls.

9. A portal apparatus for screening an object for the presence thereon of target particles, said portal apparatus comprising:

two generally vertical sides;

a transom extending substantially horizontally between the respective tops of said sides, whereby said sides and said transom define therebetween a test space;

means in said transom for generating a downward flow of air into said test space and between said sides;

a particle detector; and means for moving air from within the test space to said particle detector.

10. An apparatus according to claim 9 wherein each of said sides comprises:

a substantially vertical inside wall;

a sloped wall below and connected to said inside wall; and a substantially vertical bottom wall below and connected to said sloped wall, whereby said inside walls are spaced further apart than said bottom walls, thereby narrowing said test space from top to bottom.

11. An apparatus according to claim 9 wherein said means for generating a downward flow of air comprises at least one fan for blowing ambient air.

12. An apparatus according to claim 10 wherein said means for moving air from within the test space comprises:

a fan in at least one of said sides, and at least one vent intake disposed in at least one of said bottom walls.

13. A portal apparatus for screening an object for the presence thereon of trace amounts of a target substance, said apparatus comprising:

means for generating a downward flow of air past the object whereby particles selected from the group consisting of volatile particles of the target substance on the object which are dislodged therefrom by flow of air, non-volatile particles of the target substance on the object which are dislodged therefrom by flow of air, particles of the target substance present in air surrounding the object, and combinations thereof become entrained in the flowing air; and means for partially containing the flowing air to direct the air towards a detector.

14. An apparatus according to claim 13, wherein said means for partially containing comprises:

two upright sides in spaced-apart relation, each of said sides comprising at least one sloping wall whereby the distance separating said sides decreases from the tops of said sides to the bottoms of said sides;

a transom extending substantially horizontally between and connecting respective tops of said sides, whereby said sides and said transom define therebetween a test space.

15. An apparatus according to claim 14 wherein said means for generating a downward flow of air comprises a pair of fans disposed in said transom.

16. An apparatus according to claim 15 wherein each of said sides comprises:

a substantially vertical inside wall;

a sloped wall below and connected to said inside wall; and a substantially vertical bottom wall below and connected to said sloped wall, whereby said zone above the object is defined at least in part by said inside walls, and said zone below the object is defined at least in part by said bottom walls, said zone above comprising a larger volume than said zone below.

17. An apparatus according to claim 16 further comprising air jet nozzles disposed in said vertical inside walls for blowing air laterally within said test space.

18. An apparatus according to claim 17 wherein said detector comprises an ion mobility spectrometer.

19. An apparatus according to claim 18 further comprising:

a fan in at least one of said sides; and at least one vent intake disposed in at least one of said bottom walls.

20. An apparatus for screening an object for the presence of a target substance thereon, comprising:

a detector;

means for generating a predominantly uni-directional flow of air from a zone of relative higher pressure located in a first location in relation to the object to a zone of relative lower pressure located in a second location in relation to the object, said first location being different from said second location, said flow of air passing in close proximity to the object whereby particles selected from the group consisting of volatile particles of the target substance on the object which are dislodged therefrom by flow of air, non-volatile particles of the target substance on the object which are dislodged therefrom by flow of air, particles of the target substance present in air surrounding the object, and combinations thereof become entrained in the flowing air; and means for moving the air with entrained particles from the zone of relative lower pressure to the detector.

21. An apparatus according to claim 20 wherein said detector comprises an ion mobility spectrometer.

22. An apparatus according to claim 20 further comprising means for partially containing the flow of air from the zone of relative higher pressure to the zone of relative lower pressure.

23. A portal apparatus for screening an object for the presence thereon of trace amounts of a target substance, said apparatus comprising:

means for generating a predominantly uni-directional flow of air, said flow of air passing in close proximity past the object from a zone of relative higher pressure to a zone of relative lower pressure whereby particles selected from the group consisting of volatile particles of the target substance on the object which are dislodged therefrom by flow of air, non-volatile particles of the target substance on the object which are dislodged therefrom by flow of air, particles of the target substance present in air surrounding the object, and combinations thereof become entrained in the flowing air; and means for moving the air with entrained particles from the zone of relative lower pressure to a detector.

* * * * *